United States Patent
Schmid et al.

(10) Patent No.: US 6,878,696 B2
(45) Date of Patent: Apr. 12, 2005

(54) PROCESS FOR THE STABILIZATION OF ACYLGLYCEROLS COMPRISING HIGH AMOUNTS OF ω-3 POLYUNSATURATED FATTY ACIDS BY MEANS OF γ-CYCLODEXTRIN

(75) Inventors: Gerhard Schmid, Ann Arbor, MI (US); Mark Harrison, Ann Arbor, MI (US); Pat Polchniski, Tecumseh, MI (US)

(73) Assignee: Wacker BioChem Corporation, Adrian, MI (US)

( * ) Notice: Subject to any disclaimer, the term of this patent is extended or adjusted under 35 U.S.C. 154(b) by 78 days.

(21) Appl. No.: 10/304,901

(22) Filed: Nov. 26, 2002

(65) Prior Publication Data

US 2003/0087879 A1 May 8, 2003

Related U.S. Application Data

(63) Continuation of application No. 09/501,933, filed on Feb. 10, 2000, now abandoned.

(30) Foreign Application Priority Data

Apr. 1, 1999 (EP) .............................. 99106106

(51) Int. Cl.$^7$ .................. A01N 43/04; A61K 31/715
(52) U.S. Cl. .................. 514/58; 514/23; 536/103; 536/123.1; 536/124
(58) Field of Search .................. 514/23, 58; 536/103, 536/124, 123.1

(56) References Cited

U.S. PATENT DOCUMENTS

| 4,775,749 A | 10/1988 | Hijiya et al. |
|---|---|---|
| 4,777,162 A | 10/1988 | Hijiya et al. |
| 4,831,022 A | 5/1989 | Hijiya et al. |
| 5,189,149 A | 2/1993 | Bruzzese et al. |

FOREIGN PATENT DOCUMENTS

| CA | 2 246 282 | 10/1997 |
|---|---|---|
| DE | 196 12 658 A1 | 10/1997 |
| EP | 0 470 452 A2 | 7/1991 |
| GB | 2 146 650 A | 4/1985 |
| WO | WO 98/18610 | 5/1998 |

OTHER PUBLICATIONS

Determination of the Oxidative Stability Of Fats and Oils: Comparison Between the Active Oxygen Method (AOCS Cd 12–57) and The Rancimat–Method, 792–795 (1986), Laubli et al.

*Primary Examiner*—James O. Wilson
*Assistant Examiner*—Patrick Lewis
(74) *Attorney, Agent, or Firm*—Brooks Kushman P.C.

(57) ABSTRACT

A method to stabilize acylglycerols comprising ω-3 polyunsaturated fatty acids against oxidative degradation characterized in that γ-cyclodextrin is mixed either batchwise or continuously with the acylglycerol comprising ω-3 polyunsaturated fatty acids, thus forming a γ-CD/acylglycerol complex.

11 Claims, No Drawings

PROCESS FOR THE STABILIZATION OF ACYLGLYCEROLS COMPRISING HIGH AMOUNTS OF ω-3 POLYUNSATURATED FATTY ACIDS BY MEANS OF γ-CYCLODEXTRIN

This is a continuation of application(s) Ser. No. 09/501,933 filed on Feb. 10, 2000 now abandoned, and to European application 99 106 106.0 filed on Apr. 1, 1999.

TECHNICAL FIELD

The invention relates to processes for the stabilization of acylglycerols comprising high amounts of ω-3 polyunsaturated fatty acids by means of γ-cyclodextrin, to the complexes thus prepared, and to their use.

BACKGROUND ART

Cyclodextrins are cyclic oligosaccharides which consist of 6, 7 or 8 α(1–4)-linked anhydroglucose units. The α-, β- or γ-cyclodextrins, which are prepared, for example, by enzymatic starch conversion, differ in the diameter of their hydrophobic cavity and are generally suitable for the inclusion of a large number of lipophilic substances.

Acylglycerols comprising high amounts of ω-3 polyunsaturated fatty acids, for example eicosapentaenoic acid (EPA), docosahexaenoic acid (DHA), docosatetraenoic acid (DTA), or docosapentaenoic acid (DPA), are employed in the food and dietary supplement sector to provide essential fatty acids. Essential fatty acids have been linked to the overall health and wellbeing of humans and to the treatment and prevention of diseases associated with the cardiovascular system, inflammatory disorders, human development, fitness, and performance.

The limited stability of ω-3 polyunsaturated glycerol esters discourages their wider use. This instability results from enhanced sensitivity to oxidative decomposition (e.g. by exposure to light, atmospheric oxygen, heat or microorganisms) due to the large number of carbon carbon (C—C) double bonds. Autoxidation takes place at the C—C double bond, which leads primarily to the formation of peroxides, and then to aldehydes, ketones and acids. Secondary reactions involve isomerizations and polymerizations.

U.S. Pat. No. 5,189,149 discloses a method of producing complexes of long chain polyunsaturated fatty acids, their salts and esters inclusive of fish and vegetable oil glycerides, with α-, β- and γ-cyclodextrin (α-, β- and γ-CD) and hydroxypropyl-β-cyclodextrin, and the resulting complexes. This patent does not disclose the composition of their resulting complexes, or their stability.

U.S. Pat. Nos. 4,831,022; 4,777,162; and 4,775,749 disclose inclusion compounds of eicosapentaenoic acid and γ-cyclodextrin and food products containing the inclusion compound. These patents teach that the complex has the highest eicosapentaenoic acid content when γ-CD is used as cyclodextrin. The patents further disclose the high stability of the eicosapentaenoic acid/γ-cyclodextrin complex. The patents do not disclose complexes of derivatives of eicosapentaenoic acid or other ω-3 polyunsaturated fatty acids with γ-CD.

DISCLOSURE OF INVENTION

It is an object of the present invention to provide a method to stabilize acylglycerol comprising ω-3 polyunsaturated fatty acids against oxidative degradation. These and other objects are achieved by a method in which γ-cyclodextrin is mixed with acylglycerol comprising ω-3 polyunsaturated fatty acids, either batchwise or continuously thus forming a γ-CD/acylglycerol complex. The batches are mixed vigorously, i.e. kneaded or stirred vigorously, depending on the consistency. The use of γ-cyclodextrin surprisingly allows better stabilization of the acylglycerols comprising ω-3 polyunsaturated fatty acids than the use of α- or β-cyclodextrin.

DESCRIPTION OF THE PREFERRED EMBODIMENTS

Preparation of the subject invention compositions from concentrated aqueous γ-CD solutions has proved advantageous. The acylglycerols comprising ω-3 polyunsaturated fatty acids are added to the aqueous γ-CD solution. The CD concentration of the aqueous solution before the addition of acylglycerol is preferably between 5 and 60% by weight. A CD concentration of 10–40% by weight is especially preferred.

The weight ratio of acylglycerols comprising ω-3 polyunsaturated fatty acids to CD is preferably between 0.1:1 and 5:1, especially preferably between 0.4:1 and 3:1.

The mixing of acylglycerol and γ-CD is preferably effected in a temperature range from above freezing point to 80° C. The process is most preferably carried out at 10–60° C., particularly at approximately 15–50° C. The mixing time depends on the temperature and is preferably between one hour and a few days. As a rule, a mixing time of 10 to 30 hours will suffice.

Complexing is preferably effected under atmospheric pressure. Complexing is preferably effected under a protective gas atmosphere (nitrogen or argon).

According to the present invention, "acylglycerol comprising ω-3 polyunsaturated fatty acids" preferably is a mono-, di-, tri-acyl glycerol, alkyl modified glycerol, or glycerol mono-phosphate, comprising at least 1 ω-3 polyunsaturated fatty acid. "ω-3 polyunsaturated fatty acid" is preferably a residue selected from the group EPA, DHA, DTA or DPA.

The especially prefered meaning of acylglycerol comprising ω-3 polyunsaturated fatty acid is mono-, di-, or tri-acylglycerol or glycerol mono-phospate, with at least 1 EPA or DHA residue.

The most preferred meaning of acylglycerol comprising ω-3 polyunsaturated fatty acid is mono, di, tri-, acylglycerol comprising at least 1 EPA residue, preferably in the amount of 5–30%, or at least 1 DHA residue, preferably in the amount of 5–30%.

The composition of the ω-3 polyunsaturated fatty acids of the acylglycerols can be determined in a known manner by gas chromatographic analysis of the corresponding methyl esters.

The acylglycerols comprising ω-3 polyunsaturated fatty acids are obtained in a manner known per se, for example by wet rendering, often followed by continuous centrifugal separation of the fatty and aqueous phases. Open hydraulic presses, cage presses and continuous screw presses are all used in the final recovery of oil from the rendering residues, and the latter are often solvent extracted after pressing.

Surprisingly, it has been discovered that acylglycerols comprising ω-3 polyunsaturated fatty acids can be stabilized in an outstanding manner by complexation with γ-cyclodextrin, especially at EPA and/or DHA concentrations between 15% and 40% (by weight). A markedly higher stabilization of the unsaturated compounds was found in comparison with α- and β-cyclodextrin. When tested using a Rancimat machine the γ-CD/acylglycerol complexes showed a much higher stability than those obtained with α- and β-CD. The Gamma cyclodextrin complexes of acylglycerols comprising ω-3 polyunsaturated fatty acids have a stability time on the Rancimat machine (Induction Time) in excess of 24 hours at 100° C.

The invention therefore also relates to a complex of γ-CD and acylglycerols comprising ω-3 polyunsaturated fatty acids. A complex according to the invention consists of Gamma cyclodextrin comprising preferably 5–50% by weight of acylglycerols comprising ω-3 polyunsaturated fatty acids. Preferred is a content of 15%–40% by weight of acylglycerols comprising ω-3 polyunsaturated fatty acids.

The acylglycerols comprising ω-3 polyunsaturated fatty acids are preferably mono, di or triacylglycerols comprising at least 1 EPA in a preferred content of 5–30%, or at least 1 DHA residue, in a preferred content of 5–30%. The complexes, which are sparingly soluble in water, can be used directly in the form of the reaction mixture. Alternatively, they can be isolated and processed by filtration, centrifugation, drying, grinding, sieving, screening, granulating or tableting to suit the procedure which is customary in each case.

The complexes according to the present invention can be used, for example, in the food or dietary supplements sector to provide essential fatty acids. Numerous studies have linked ω-3 polyunsaturated fatty acids with the treatment and prevention of disease, especially of the cardiovascular system, and Inflammatory Disorders, e.g. decreased risk of coronary heart disease, reduction in triglyceride levels, lower blood pressure, arthitis, asthma, Crohn's disease, psoriasis, in human development, especially for brain and retina growth and development, and improvements in fitness and performance, promoting aerobic endurance and mucle recovery.

The following examples are intended to illustrate the invention in greater detail.

In the examples the stability of the complexes was measured by the Rancimat method. The 679 Rancimat machine is an instrument for the determination of oxidative and thermal stabilities. It is produced and supplied by Metrohm Ltd. (CH-9101 Herisau, Switzerland). In the case of oils and fats or substances containing oils and fats, the stability towards oxidative decomposition can be determined. The 679 Rancimat comprises a control unit and a wet section for 3 or 6 reaction and measuring vessels. In the wet section, the samples are exposed to a stream of atmospheric oxygen at elevated temperature. In the case of oils and fats, this gives rise to organic acids. The volatile decomposition products are trapped in a measuring vessel filled with distilled water and continuously detected with a conductivity cell. The control unit assumes control and evaluation of the measurements running in the wet section.

The oxidative resistance of the acylglycerol/CD complexes was measured at 100° C. Evaluation was done using modes 1 (induction time) and 2 (stability time with $\Delta K$ set at 30 $\mu$S/cm). In general, evaluation mode 1 (induction time) was used. Airflow of 20 L/h was used for all samples. Sample quantities of 2.0 g (solid complex) and 3.5 g (liquid fish oil) were used.

Induction time is calculated from the curve $\kappa=f(t)$. Induction time is the time needed to reach the break point of the curve. The induction time is a characteristic of the oxidative stability of the sample under evaluation and is in almost complete agreement with the results of the time consuming AOM method. (Determination of the Oxidative Stability of Fats and Oils: Comparison between the Active Oxygen Method (AOCS Cd 12–57) and the Rancimat Method, JAOCS 63, 792–795 (1986), Läubli, M. W. and Bruttel, P. A.)

Stability Time is calculated from the curve $\kappa=f(t)$. It is the time needed to reach a preset conductivity change ($\Delta K$ set at 30 $\mu$S/cm).

EXAMPLE 1

To 150 ml of deionized and degassed water at 60° C. in a 1-L reaction kettle was added 100.0 g of dry Gamma-cyclodextrin. The reaction vessel was shielded to exclude light and once the solids had dissolved, 22.0 g of acylglycerol solution containing approx. 5% EPA and min. 25% DHA was added. The mixture was stirred under a nitrogen atmosphere at 60° C. for 24 hours then allowed to cool to ambient temperature. The resulting paste was dried under vacuum at 50° C. for 48 hours. The product was obtained as a white powder in a yield of 116.0 g (95%). Acylglycerol content: 18% by weight. Oxidation Induction time at 100° C. ($IT_{100}$): >24 hours. Stability time at 100° C.: >24 hours.

EXAMPLE 2

To 150 ml of deionized and degassed water at 20° C. in a 1-L reaction kettle was added 100.0 g of dry Gamma-cyclodextrin. The reaction vessel was shielded to exclude light then 22.0 g of acylglycerol solution containing approx. 5% EPA and min. 25% DHA was added and the mixture stirred under a nitrogen atmosphere at 20° C. for 24 hours. The solid was removed and dried under vacuum at 50° C. for 48 hours. The product was obtained as a white powder in a yield of 118.3 g (97%). Acylglycerol content: 18% by weight. Oxidation Induction time at 100° C. ($IT_{100}$): >24 hours. Stability time at 100° C.: >24 hours.

EXAMPLE 3

To 230 ml of deionized and degassed water at 40° C. in a 1-L reaction kettle was added 100.0 g of dry γ-cyclodextrin. The reaction vessel was shielded to exclude light and once the solids had dissolved, 43.0 g of acylglycerol solution containing approx. 5% EPA and min. 25% DHA was added. The mixture was stirred under a nitrogen atmosphere at 40° C. for 24 hours then allowed to cool to ambient temperature. The resulting paste was filtered to remove water then dried under vacuum at 40° C. for 48 hours. The product was obtained as a white powder in a yield of 138.2 g (97%). Acylglycerol content: 30% by weight. Oxidation Induction time at 100° C. ($IT_{100}$): >23 hours. Stability time at 100° C.: >20 hours.

EXAMPLE 4

To 230 ml of deionized and degassed water at 40° C. in a 1-L reaction kettle was added 100.0 g of dry γ-cyclodextrin. The reaction vessel was shielded to exclude light and once the solids had dissolved, 67.0 g of acylglycerol solution containing approx. 5% EPA and min. 25% DHA was added. The mixture was stirred under a nitrogen atmosphere at 40° C. for 24 hours then allowed to cool to ambient temperature. The resulting paste was filtered to remove water then dried under vacuum at 50° C. for 48 hours. The product was obtained as a white powder in a yield of 162.2 g (97%). Acylglycerol content: 40% by weight. Oxidation Induction time at 100° C. ($IT_{100}$): >9 hours. Stability time at 100° C.: >9 hours.

EXAMPLE 5

To 450 ml of deionized and degassed water at 40° C. in a Stephan Mixer was added 200.0 g of dry γ-cyclodextrin. The reaction vessel was shielded to exclude light and once the solids had dissolved, 67.0 g of acylglycerol solution containing approx. 5% EPA and min. 25% DHA was added. The mixture was stirred under a nitrogen atmosphere at 40° C. for 24 hours then allowed to cool to ambient temperature. The resulting paste was dried under vacuum at 50° C. for 48 hours. The product was obtained as a white powder in a yield of 250.4 g (94%). Acylglycerol content: 25% by weight. Oxidation Induction time at 100° C. ($IT_{100}$): >24 hours. Stability time at 100° C.: >11 hours.

EXAMPLE 6

To 230 ml of deionized and degassed water at 40° C. in a 1-L reaction kettle was added 100.0 g of dry γ-cyclodextrin. The reaction vessel was shielded to exclude light and once the solids had dissolved, 25.0 g of acylglycerol solution containing approx. 5% EPA and min. 25% DHA was added. The mixture was stirred under a nitrogen atmosphere at 40° C. for 24 hours then allowed to cool to ambient temperature. The resulting paste was filtered to remove water then dried under vacuum at 50° C. for 3 days. The product was obtained as a white powder in a yield of 121.3 g (97%). Acylglycerol content: 20% by weight. Oxidation Induction time at 100° C. ($IT_{100}$): >24 hours. Stability time at 100° C.: >24 hours.

EXAMPLE 7

To 230 ml of deionized and degassed water at 40° C. in a 1-L reaction kettle was added 100.0 g of dry γ-cyclodextrin. The reaction vessel was shielded to exclude light and once the solids had dissolved, 17.7 g of acylglycerol solution containing approx. 5% EPA and min. 25% DHA was added. The mixture was stirred under a nitrogen atmosphere at 40° C. for 24 hours then allowed to cool to ambient temperature. The resulting paste was filtered to remove water then dried under vacuum at 50° C. for 48 hours. The product was obtained as a white powder in a yield of 109.0 g (93%). Acylglycerol content: 15% by weight. Oxidation Induction time at 100° C. ($IT_{100}$): >24 hours. Stability time at 100° C.: >24 hours.

EXAMPLE 8

Comparison Example

To 50 ml of deionized and degassed water at 40° C. was added 20.0 g of dry Beta-CD. The flask was covered to exclude light then 4.4 g of acylglycerol solution containing approx. 5% EPA and min. 25% DHA was added to the slurry. The mixture was stirred under a nitrogen atmosphere at 40° C. for 4 hours then allowed to cool overnight to ambient temperature. The solid was collected by filtration and dried under vacuum at 40° C. to give 24.0 g (98%) of material as a light yellow powder. Acylglycerol content: 18% by weight. Oxidation Induction time at 100° C. ($IT_{100}$): 3.1 hours. Stability time at 100° C.: 4.4 hours.

EXAMPLE 9

Comparison Example

To 50 ml of deionized and degassed water at 40° C. was added 20.0 g of dry Alpha-CD. The flask was covered to exclude light then 4.4 g of acylglycerol solution containing approx. 5% EPA and min. 25% DHA was added to the slurry. The mixture was stirred under a nitrogen atmosphere at 40° C. for 4 hours then allowed to cool overnight to ambient temperature. The solid was collected by filtration and dried under vacuum at 40° C. to give 11.7 g (48%) of material as a light yellow powder. Acylglycerol content: 18% by weight. Oxidation Induction time at 100° C. ($IT_{100}$): 3.4 hours. Stability time at 100° C.: 4 hours.

EXAMPLE 10

Comparison Example

To 230 ml of deionized and degassed water at 40° C. in a 1-L reaction kettle was added 100.0 g of dry γ-cyclodextrin. The reaction vessel was shielded to exclude light and once the solids had dissolved, 100.0 g of acylglycerol solution containing approx. 5% EPA and min. 25% DHA was added. The mixture was stirred under a nitrogen atmosphere at 40° C. for 24 hours then allowed to cool to ambient temperature. The resulting paste was filtered to remove water then dried under vacuum at 50° C. for 48 hours. The product was obtained as a yellow-white powder in a yield of 195.07 g (97%). Acylglycerol content: 50% by weight. Oxidation Induction time at 100° C. ($IT_{100}$): 6.7 hours. Stability time at 100° C.: 6.8 hours.

EXAMPLE 11

To 250 ml of deionized and degassed water at 45° C. in a 1-L reaction kettle was added 100.0 g of dry γ-cyclodextrin. The reaction vessel was shielded to exclude light and once the solids had dissolved, 24.0 g of acylglycerol solution containing approx. 25% DHA was added. The mixture was stirred under a nitrogen atmosphere at 45° C. for 24 hours then allowed to cool to ambient temperature. The resulting paste was filtered to remove water then dried under vacuum at 50° C. for 48 hours. The product was obtained as a white powder in a yield of 123.07 g (99%). Acylglycerol content: 20% by weight. Oxidation Induction time at 100° C. ($IT_{100}$): >24 hours.

EXAMPLE 12

To 250 ml of deionized and degassed water at 45° C. in a 1-L reaction kettle was added 100.0 g of dry γ-cyclodextrin. The reaction vessel was shielded to exclude light and once the solids had dissolved, 24.0 g of acylglycerol solution containing approx. 25% EPA was added. The mixture was stirred under a nitrogen atmosphere at 45° C. for 24 hours then allowed to cool to ambient temperature. The resulting paste was filtered to remove water then dried under vacuum at 50° C. for 48 hours. The product was obtained as a white powder in a yield of 123.57 g (99%). Acylglycerol content: 20% by weight. Oxidation Induction time at 100° C. ($IT_{100}$): >24 hours.

Results:

In general, complexes of acylglycerol (25% by weight) with gamma-CD showed no oxidation over 24 hours while control samples of 18% acylglycerol mixed with alpha—or beta CD showed rapid oxidation (less than 5 hours). Complexes of acylglycerol in excess of 40% however began to exhibit oxidation.

Chart of Results

| Ex. No. | Acyl-glycerol | CD conc. (wt %) | Rxn. Temp. (C.) | Rxn. Time (hr) | Yield (%) | Induct. Time 100° C. (hr) | Stability Time (hr) |
| --- | --- | --- | --- | --- | --- | --- | --- |
| 1 | 18 | 40 | 60 | 24 | 95 | >24 | >24 |
| 2 | 18 | 40 | 20 | 24 | 97 | >24 | >24 |
| 3 | 30 | 30 | 40 | 24 | 97 | >23 | >20 |
| 4 | 40 | 30 | 40 | 24 | 97 | 9.2 | 9.0 |
| 5 | 25 | 30 | 0 | 24 | 94 | >24 | >11 |
| 6 | 20 | 30 | 40 | 24 | 97 | >24 | >24 |
| 7 | 15 | 30 | 40 | 24 | 93 | >24 | >24 |
| 8* | 18 | 28 | 40 | 24 | 99 | 3.1 | 4.4 |
| 9* | 18 | 28 | 40 | 24 | 48 | 3.4 | 4 |
| 10* | 50 | 30 | 40 | 24 | 97 | 6.7 | 6.8 |
| 11 | 20 | 30 | 45 | 24 | 99 | >24 | n.d. |
| 12 | 20 | 30 | 45 | 24 | 99 | >24 | n.d. |
| Acyl-glycerol | 100 | — | — | — | — | 5 | 4 |
| Acyl-glycerol/γ-CD Mixture | ~20 | — | — | — | — | 3.3 | 4 | n.d. = not determined
*= comparative examples

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A complex of γ-cyclodextrin and from about 5 to 50 weight percent of at least one glycerol triester comprising ω-3 polyunsaturated fatty acids, said weight percent based upon the total weight of the γ-cyclodextrin and glycerol triester complex, the γ-cyclodextrin and glycerol triester complex having a higher thermal oxidative stability as measured by induction time at 100° C. than uncomplexed acyl glycerol triester and complexes of acyl glycerol triester with either α-cyclodextrin or β-cyclodextrin.

2. The complex of claim 1, comprising from 15 to 40 weight percent of glycerol triester.

3. The complex of claim 1, wherein said ω-3 polyunsaturated fatty acids are selected from the group consisting of eicosopentaenoic acid, docosahexaenoic acid, docosatraenoic acid, docosapentaenoic acid, and mixtures thereof.

4. The complex of claim 2, wherein said ω-3 polyunsaturated fatty acids are selected from the group consisting of eicosopentaenoic acid, docosahexaenoic acid, docosatraenoic acid, docosapentaenoic acid, and mixtures thereof.

5. The complex of claim 1, wherein are glycerol triester contains a phosphate ester moiety.

6. A process for the preparation of the complex of claim 1, comprising mixing γ-cyclodextrin with said glycerol triester, forming a γ-cyclodextrin/glycerol triester complex.

7. The process of claim 6, wherein said glycerol triester is added to an aqueous γ-cyclodextrin solution.

8. The process of claim 7 wherein the concentration of γ-cyclodextrin in said solution prior to addition of glycerol triester is between 5 and 60% by weight based on the weight of the solution.

9. The process of claim 7 conducted at a temperature of above the freezing point of the γ-cyclodextrin solution to about 80° C.

10. The process of claim 7, conducted in an inert gas atmosphere.

11. A food or dietary supplement comprising the complex of claim 1.

* * * * *

UNITED STATES PATENT AND TRADEMARK OFFICE
CERTIFICATE OF CORRECTION

PATENT NO.    : 6,878,696 B2
DATED         : April 12, 2005
INVENTOR(S)   : Gerhard Schmid et al.

It is certified that error appears in the above-identified patent and that said Letters Patent is hereby corrected as shown below:

<u>Title page,</u>
Item [75], Inventor, delete "Pat Polchniski" and insert therefor: -- Pat Polchinski --.

Signed and Sealed this

Twelfth Day of July, 2005

JON W. DUDAS
*Director of the United States Patent and Trademark Office*